US009814812B2

(12) United States Patent
Scheidegger et al.

(10) Patent No.: US 9,814,812 B2
(45) Date of Patent: Nov. 14, 2017

(54) BREAST PUMP

(71) Applicant: BAMED AG, Wollerau (CH)

(72) Inventors: Andreas Scheidegger, Konolfingen (CH); Beatrice Glatz, Konolfingen (CH)

(73) Assignee: BAMED AG, Wollerau (CH)

( * ) Notice: Subject to any disclaimer, the term of this patent is extended or adjusted under 35 U.S.C. 154(b) by 557 days.

(21) Appl. No.: 14/360,463

(22) PCT Filed: Nov. 20, 2012

(86) PCT No.: PCT/EP2012/073057
§ 371 (c)(1),
(2) Date: May 23, 2014

(87) PCT Pub. No.: WO2013/076055
PCT Pub. Date: May 30, 2013

(65) Prior Publication Data
US 2014/0330200 A1 Nov. 6, 2014

(30) Foreign Application Priority Data
Nov. 23, 2011 (EP) .................................. 11190314

(51) Int. Cl.
*A61M 1/06* (2006.01)
(52) U.S. Cl.
CPC .............. *A61M 1/064* (2014.02); *A61M 1/06* (2013.01); *A61M 1/066* (2014.02)

(58) Field of Classification Search
CPC ...... A61M 1/064; A61M 1/06; A61M 1/1039; A61M 2025/1022; A61M 1/066; F04B 43/12

See application file for complete search history.

(56) References Cited

U.S. PATENT DOCUMENTS

| | | | |
|---|---|---|---|
| 3,366,071 A * | 1/1968 | Dutler | F04B 43/12 417/477.6 |
| 5,924,852 A * | 7/1999 | Moubayed | A61M 5/14228 417/474 |
| 6,004,288 A | 12/1999 | Hochstedler et al. | |

(Continued)

FOREIGN PATENT DOCUMENTS

| | | |
|---|---|---|
| DE | 2207887 A1 | 8/1973 |
| DE | 202005019583 U1 | 2/2006 |

(Continued)

OTHER PUBLICATIONS

Japanese Office Action dated May 23, 2016; Appln. No. 2014-542795.

(Continued)

*Primary Examiner* — Emily Schmidt
*Assistant Examiner* — Lauren M Peng
(74) *Attorney, Agent, or Firm* — Ladas & Parry LLP

(57) ABSTRACT

A breast pump for collecting breast milk having a funnel intended to receive the breast, a housing and a device for producing a negative pressure. The funnel consists of a flexible material and extends into the housing. The device for producing a negative pressure has at least one body that is movable over a portion of the length of the funnel while compressing the funnel.

21 Claims, 2 Drawing Sheets

(56) References Cited

U.S. PATENT DOCUMENTS

| | | | | |
|---|---|---|---|---|
| 2006/0270973 A1* | 11/2006 | Chu | ............... | A61H 9/0078 604/74 |
| 2007/0060873 A1* | 3/2007 | Hiraoka | ............ | A61M 1/0066 604/74 |
| 2007/0219486 A1 | 9/2007 | Myers et al. | | |
| 2008/0167605 A1* | 7/2008 | Torvik | ............... | A61M 1/06 604/74 |
| 2010/0130921 A1* | 5/2010 | Kobayashi | ............ | A61M 1/06 604/74 |

FOREIGN PATENT DOCUMENTS

| | | |
|---|---|---|
| EP | 1 661 590 A1 | 5/2006 |
| EP | 2 111 882 A1 | 10/2009 |
| JP | 48-66204 A | 9/1973 |
| JP | 2005-279044 A | 10/2005 |
| JP | 2008-183143 A | 8/2008 |
| JP | 2008-237522 A | 10/2008 |
| WO | 03/028616 A2 | 4/2003 |

OTHER PUBLICATIONS

International Search Report dated Nov. 2, 2013; PCT/EP2012/073057.

EPO Office Action dated Nov. 5, 2012; Appln. No. 11190314.2-1257.

* cited by examiner

BREAST PUMP

BACKGROUND OF THE INVENTION

The invention relates to a breast pump for collecting breast milk, comprising a funnel intended to receive the breast, a housing, and a device for producing a pumping effect.

Pumping breast milk and storing it for short periods allows breastfeeding mothers to be autonomous and independent and to go to work. Therefore, many different breast pumps have been developed, practically all of which use pulsating negative pressure. More specifically, the pressure is mostly lowered by 60 to 120 mbar at 1 to 2 Hz by means of a diaphragm pump. The pump is connected via a tube to the interior of a collecting container similar to a baby bottle. The container has a funnel-shaped opening that is held against the breast. By the negative pressure, the nipple is aspired into the funnel in a pulsating manner, thereby producing a pumping effect on the areola in which the milk collects and is drawn through the nipple by the negative pressure.

One disadvantage of known breast pumps is the noise generated by the pulsating negative pressure, which many users find annoying.

Another disadvantage of many known breast pumps is the fact that the described suction and extension of the nipple produces friction between the latter and the funnel, which is found displeasing and may cause irritations. In several known breast pumps it is attempted to alleviate this disadvantage by incorporating cushion-like hollow bodies in the suction funnel and rhythmically supplying a fluid thereto, thus imparting a massage movement to the breast. In this manner it is attempted to imitate the jaw movements of the baby in the funnel portion. As a result, a smaller negative pressure may possibly be used.

Furthermore, practically all known breast pumps have the disadvantage of being composed of a large number of components, most of which have to be cleaned also. Although they may mostly be easy to handle, the appliances are relatively bulky, which is a hindrance particularly with regard to their transport e.g. in a handbag.

On account of the aforementioned disadvantages and of the fact that in known breast pumps the pumping process substantially differs from the natural sucking of a baby, many women find breast milk pumping displeasing and therefore prematurely discontinue feeding their babies with breast milk.

On the background of this prior art, the invention is based upon the object of suggesting a breast pump that does not suffer from the aforementioned disadvantages and more particularly is gentle to the breast in operation, better imitates the drinking and swallowing of a baby, whose design is simple and compact, and that is easy to clean.

BRIEF SUMMARY OF THE INVENTION

According to the invention, this object is attained in that the funnel consists of a flexible material and extends into the housing, and in that for producing a pumping effect, the device comprises at least one body that is movable over a portion of the length of the funnel while compressing the funnel.

In particular, this solution according to the invention offers the advantage that via the flexible funnel, the aforementioned body compresses the breast received therein in a wavelike manner, on one hand, and on the other hand, confers the funnel the function of a hose pump. In this manner, the breast pump of the invention comes very close in its function to the natural sucking behavior of an infant.

According to one embodiment, the funnel has a tubular prolongation at its narrow end. As a result of the movements of the body, this prolongation fulfills the function of a hose pump. The funnel is preferably made in one piece with its tubular prolongation, thereby making the manufacture, the assembly and disassembly, and cleaning of the funnel particularly simple.

According to another embodiment, between the wide portion of the funnel and the housing, a space is arranged that is preferably filled with a soft material or a fluid. This space is intended to imitate the soft part of a baby's palate and may e.g. be padded with a soft material, e.g. a foam material, or filled with a fluid.

According to another embodiment, the body is cam-shaped and rotatable around a rotation axis. A breast pump of this kind is particularly simple and inexpensive to manufacture.

According to another embodiment, the body is shaped as a roll that is supported such that its axis is rotatable on a circular path around a rotation axis. This measure allows a low-friction operation of the breast pump.

According to a further embodiment, the roll is designed as a planet wheel that rotates around a sun wheel arranged on the rotation axis. In this manner, the breast pump can be driven with a relatively low torque.

According to a further embodiment, two or three bodies are provided. This measure increases the efficiency of the breast pump insofar as multiple wavelike movements and pump movements per rotation are performed.

In another embodiment, the body or the bodies, respectively, are surrounded by a flexible band. This reduces the friction applied to the funnel by the body or the bodies, respectively.

According to a further embodiment, the band is connected on part of its length to the funnel. In this manner it is avoided that the band moves along the funnel and rubs against the latter.

According to a further embodiment, the breast pump includes a milk container that is removably connected to the funnel by means of a coupling device. A removable milk container facilitates cleaning the breast pump and allows designing and using the milk container as a baby bottle.

According to a particular embodiment, the milk container is designed as a flexible pouch. In this manner, the contact of pumped breast milk with air is avoided and the milk container need not be vented.

According to another embodiment the milk container is designed as a preferably threaded bottle. This allows using commercially available baby bottles.

According to a further embodiment the housing is openable, more particularly dividable or folding. In particular, this makes the breast pump easier to clean.

According to a further embodiment, means for manually actuating the body are provided. In this manner, the breast pump is not only particularly simple and inexpensive but the user may furthermore choose the speed of the body movement that is most agreeable to her in an advantageous manner by herself.

Alternatively or in addition to the aforementioned means, according to a further embodiment, the breast pump may comprise means for a motorized actuation of the body. These means increase the ease of use of the breast pump.

According to further embodiments, means are provided by which the negative pressure generated in operation is variable and/or by which the intensity of the wave movement produced in the funnel by the at least one body is variable.

The two last mentioned measures enable the user to adapt the mode of operation of the breast pump to her needs.

Exemplary embodiments of the invention will be explained in more detail hereinafter by way of examples with reference to the accompanying drawing showing

DETAILED DESCRIPTION OF THE INVENTION

Figure 1:
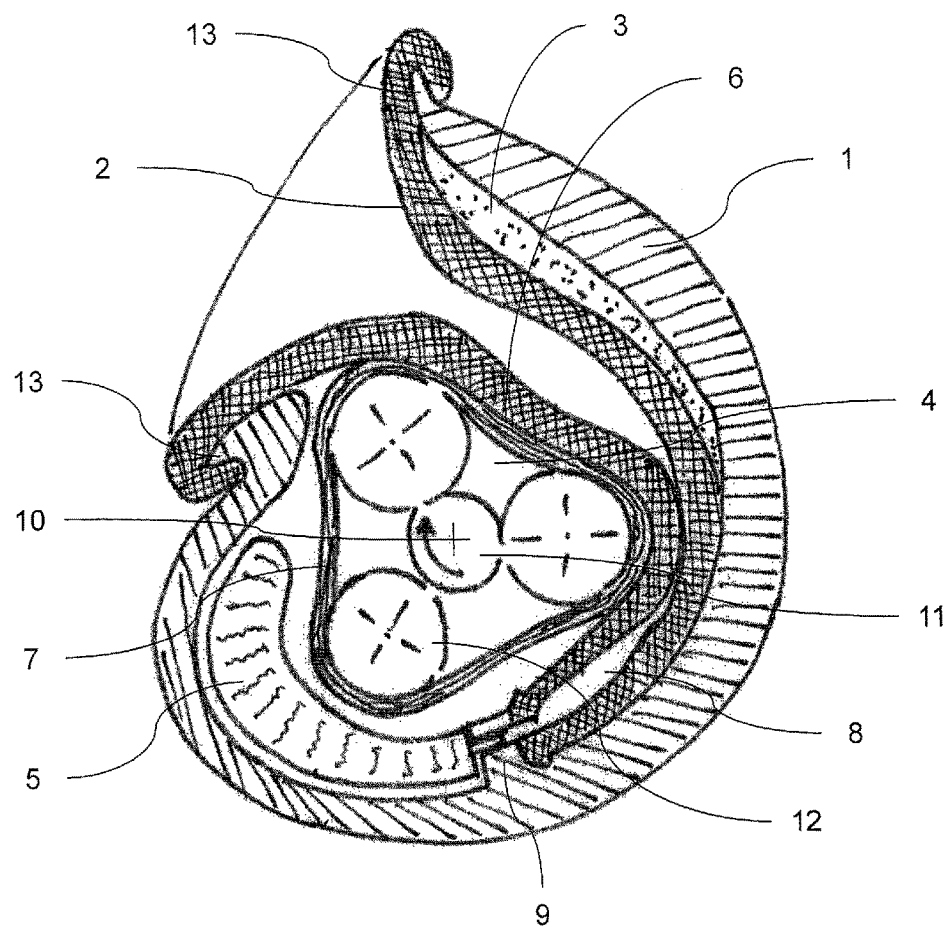
FIG. 1 a sectional view of a breast pump.

The single FIG. 1 shows an exemplary embodiment of the breast pump of the invention in a sectional view. A housing 1 has a spiral-shaped peripheral wall and is preferably designed so as to be openable in order to remove the components arranged therein for cleaning purposes. Thus, housing 1 may e.g. be dividable in a plane parallel to the drawing plane and the two housing halves may be connected to one another by a hinge. In housing 1, a funnel 2 of a soft elastic material such as silicone is arranged. Funnel 2 is mounted by its wide opening onto a circumferential housing edge 13 and from there narrows into the interior of housing 1 down to a coupling section 9 that will be discussed in more detail below. Advantageously, the cross-section of funnel 2 remains constant in the last section up to its inner end. Consequently it can be said that this last section of funnel 2 is tubular. In the area of the opening of funnel 2, between the latter and housing 1, a pressure chamber 3 is arranged. This pressure chamber 3 is intended to imitate the area of baby's palate known as the comfort zone in the technical jargon. To this end, pressure compartment 3 may be padded with a soft material, e.g. a foam material, or filled with a fluid. Funnel 2 has a dual function, namely, on one hand, that of a baby's palate and tongue applying a wave-shaped compression movement to the breast that is directed away from the latter, and on the other hand, that of a pump as it is known under the terms "hose pump" or "flexible tube pump" or "peristaltic pump". Different funnels 2 that are adapted to the shape of the user's breast can be employed in the breast pump. Moreover, funnel 2 may comprise zones of different elasticity so as to best imitate the palate of a baby. These zones may differ in the composition of the material of funnel 2 and/or in wall thickness.

Both of the aforementioned functions of funnel 2 are fulfilled by a suction gear mechanism 4 which in the depicted example is designed as a planetary gear. A sun wheel 11 rotates around a central rotation axis 10 in the direction indicated by an arrow. Sun wheel 11 may be motor-driven or manually actuated, e.g. by means of a crank handle. As a motor, an electric motor is particularly suitable, but other motor drives such as e.g. a hydraulic or a pneumatic motor may also be contemplated. In the example, three planet wheels 12 are arranged around sun wheel 11, whose axles may be arranged on a carrier (not shown) that is rotatable around rotation axis 10 and may e.g. be designed in the manner of a disk or a star. In the depicted exemplary embodiment, planet wheels 12 are surrounded in a loop-like manner by an endless, flexible pump diaphragm 7 on whose inner surface planet wheels 12 are rolling. Pump diaphragm 7 may consist of a foil, a tissue, a non-woven material, or the like. Pump diaphragm 7 is connected on a section thereof to funnel 2 by a connection 6 so that pump diaphragm 7 cannot be dislocated relative to funnel 2. It has been discovered that the intensity of the wave movement and of the negative pressure in funnel 2 can be varied by varying the tension of pump diaphragm 7. The tension of the pump diaphragm can e.g. be varied by an adjustable tensioning member (not shown) that is adjustable radially in the direction of rotation axis 10. Funnel 2 is locally compressed by planet wheel 12 located at the top in the illustration of FIG. 1 so that a closed pumping space 8 is created towards the end of funnel 2. By the rolling movement of sun wheels 12, pumping space 8 is compressed so that its content is pumped through coupling section 9 into milk container 5. At the same time, with the funnel being held against the breast, a negative pressure is created in the entrance area thereof which increases as suction gear mechanism 4 continues to rotate and draws the nipple into funnel 2. The nipple will thus enter into the range of movement of planet wheels 12 which as a result will compress and massage the nipple in a wavelike movement and thus stimulate the milk flow. At the same time, the milk flow is assisted by the negative pressure in funnel 2. Besides the aforementioned tension in pump diaphragm 7, the negative pressure created in funnel 2 during the operation of the breast pump is also variable by the choice of the material of funnel 2 and the cross-sectional shape and dimension of pumping space 8 and by the positions of planet wheels 12 relative to pumping space 8.

Milk container 5 may be designed as a rigid or flexible container and may be arranged inside or outside housing 1. A flexible, pouch-like milk container 5 has the advantage that no air needs to be displaced while it is being filled. This is not only advantageous from a hygienic point of view but also allows the breast pump to be operated independently of its position without the risk of spilling milk from milk container 5. Coupling section 9 may e.g. be designed as a simple tubular plug-on coupling onto which the milk container is pushed with a portion of the container that has an opening. Milk container 5 may also be a commercially available baby bottle that is screwed on.

The circumferential surfaces of planet wheels 12 may be shaped concavely in order to even better imitate the massaging movement of a baby's tongue. The contact between sun wheel 11 and planet wheels 12 may be frictional, or the circumferential surfaces of the wheels may be toothed. In a simpler embodiment, suction gear mechanism 4 may include rolls arranged at the free ends of arms which rotate around rotation axis 10 without the aid of a sun wheel, the rolls rolling off on the inside of pump diaphragm 7. In an even simpler embodiment, the free ends of the arms may slide on the inner surface of pump diaphragm 7 without rolls. Alternatively, instead of the arms, a cam-like body may be provided.

Funnel 2 may have nearly any desired shape and its geometry and dimensions are advantageously shaped similarly to the area of a baby's palate. During the operation of the breast pump, only funnel 2, milk container 5, and possibly a part in coupling section 9 come into contact with breast milk, thereby making the breast pump very easy to clean.

Figure 2:
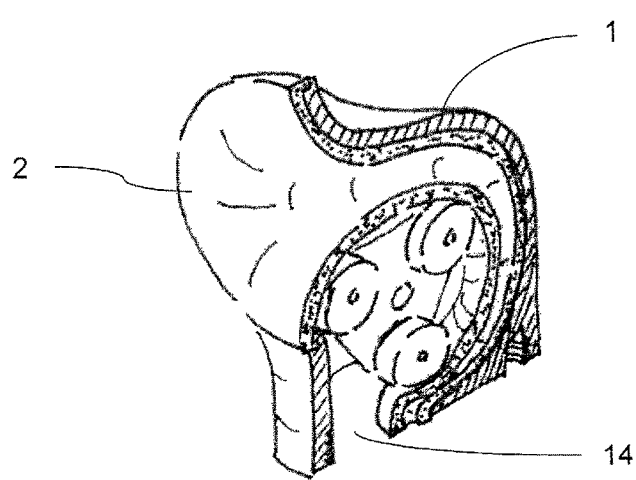
FIG. 2 a sectioned perspective view of another embodiment of the breast pump on a smaller scale than in FIG. 1, FIG. 3 a schematic perspective view of a crank handle actuated breast pump, and FIG. 4 a schematic perspective view of a motor driven breast pump with a control unit.

FIG. 2 shows a sectioned perspective view of another embodiment of the breast pump of the invention. The Figure illustrates that pressure compartment 3 can be omitted so that funnel 2 is in direct contact with housing 1. Furthermore, in this embodiment, housing 1 comprises no milk container 5 but an alternative coupling section 14 for attaching a commercially available baby bottle, e.g. by a screw coupling.

Figure 3:
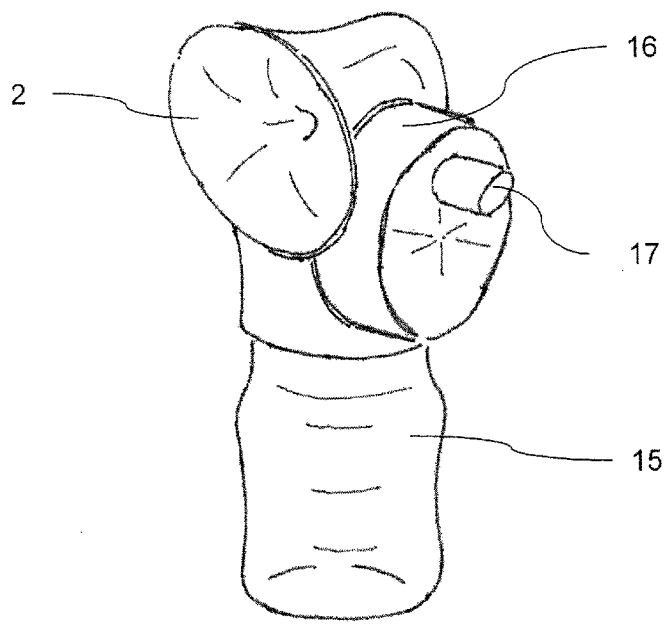

FIG. 3 shows an embodiment of the breast pump that is manually actuated. To this end, a crank handle 17 is arranged in a housing part 16. Milk container 15 is in the form of a commercially available baby bottle and received in coupling section 14 (see FIG. 2).

Figure 4:
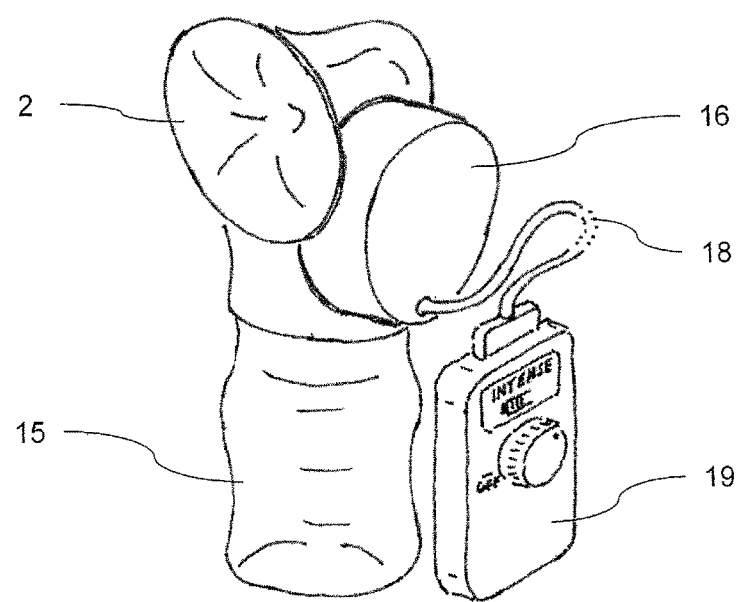

FIG. 4 shows a motor-driven, e.g. electrically operated embodiment of the breast pump. A motor (not shown) is accommodated in a housing part 16, and a control unit 19 is connected to the motor by a cable 18.

LIST OF REFERENCE NUMERALS

1 Housing
2 Funnel
3 Pressure compartment
4 Suction gear mechanism
5 Milk container
6 Connection
7 Pump diaphragm
8 Pumping space
9 Coupling section
10 Rotation axis
11 Sun wheel
12 Planet wheel
13 Housing edge
14 Coupling section
15 Milk container
16 Housing part
17 Crank handle
18 Cable
19 Control unit
20

The invention claimed is:

1. Breast pump for collecting breast milk, comprising:
a funnel intended to receive the breast,
a housing and
a device for producing a pumping effect,
wherein said funnel consists of a flexible material and has a wide portion and a narrow end and extends into the housing and for producing a pumping effect, the device comprises at least one body that is movable over a portion of the length of the funnel while compressing the funnel such that the funnel together with the movable body functions as a peristaltic pump, and
wherein the at least one body is configured to locally compress the funnel so that two opposite walls of the funnel are touching, thereby creating a closed pumping space within the funnel, wherein by movement of said body a content of said closed pumping space may be pumped through the funnel.

2. Breast pump according to claim 1, wherein said funnel has a tubular prolongation at its narrow end.

3. Breast pump according to claim 2, wherein said funnel is made in one piece with its tubular prolongation.

4. Breast pump according to claim 1 wherein between the wide portion of the funnel and the housing a space is arranged that is preferably filled with a soft material or a fluid.

5. Breast pump according to claim 1 wherein said body has a cam-like design and is rotatable around a rotation axis.

6. Breast pump according to claim 1 wherein said body is designed as a roll that is supported such that its axis is rotatable on a circular path around a rotation axis.

7. Breast pump according to claim 6, wherein said roll is designed as a planet wheel that rotates around a sun wheel arranged on the rotation axis.

8. Breast pump according to claim 1, wherein two or three bodies are provided.

9. Breast pump according to claim 1 wherein the body or bodies respectively, are surrounded by a flexible band.

10. Breast pump according to claim 9, wherein said band is connected on part of its length to the funnel.

11. Breast pump according to claim 1 further comprising a milk container that is removably connected to the funnel by means of a coupling device.

12. Breast pump according to claim 11, wherein said milk container is designated as a flexible pouch.

13. Breast pump according to claim 11, wherein said milk container is designed as a preferably threaded bottle.

14. Breast pump according to claim 1 wherein said housing is openable.

15. Breast pump according to claim 14 wherein said housing is dividable.

16. Breast pump according to claim 14 wherein said housing is foldable.

17. Breast pump according to claim 1 further comprising means for manually actuating the body.

18. Breast pump according to claim 1 further comprising means for a motorized actuation of the body.

19. Breast pump according to claim 1 wherein negative pressure is generated in operation of said pump, and means are provided by which the negative pressure generated in operation is variable.

20. Breast pump according to claim 1 wherein wave movement is produced in the funnel and means are provided by which the intensity of the wave movement produced in the funnel by the at least one body is variable.

21. Breast pump according to claim 1, wherein the at least one body is movable in a direction away from an opening of the funnel, wherein said opening is configured to receive the breast.

\* \* \* \* \*